US00PP30767P2

(12) United States Plant Patent
Sasaoka

(10) Patent No.: US PP30,767 P2
(45) Date of Patent: Jul. 30, 2019

(54) ***CATHARANTHUS* PLANT NAMED 'ELD STJARNA'**

(50) Latin Name: *Catharanthus roseus*
Varietal Denomination: Eld Stjarna

(71) Applicant: Gyosuke Sasaoka, Nara (JP)

(72) Inventor: Gyosuke Sasaoka, Nara (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 15/732,948

(22) Filed: Jan. 12, 2018

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
See application file for complete search history.

*Primary Examiner* — Anne Marie Grunberg
(74) *Attorney, Agent, or Firm* — C. A. Whealy

(57) ABSTRACT

A new and distinct cultivar of *Catharanthus* plant named 'Eld Stjama', characterized by its compact, semi-upright and uniformly mounding plant habit; vigorous growth habit; freely basal branching habit; freely flowering habit; long flowering period; relatively small star-shaped red purple-colored flowers that become light red with development; and good garden performance.

1 Drawing Sheet

Botanical designation: *Catharanthus roseus.*
Cultivar denomination: 'ELD STJARNA'.

BACKGROUND OF THE INVENTION

The present invention relates to a new and distinct *Catharanthus* plant, botanically known as *Catharanthus roseus* and hereinafter referred to by the cultivar name 'Eld Stjarna'.

The new *Catharanthus* plant is a naturally-occurring branch mutation of a proprietary selection of *Catharanthus roseus* identified as code designation MP-mtl, not patented. The new *Catharanthus* plant was discovered and selected by the Inventor on a single flowering plant of the proprietary selection in a controlled greenhouse environment in Uda, Nara, Japan in July, 2012.

Asexual reproduction of the new *Catharanthus* plant by vegetative tip cuttings in a controlled greenhouse environment in Uda, Nara, Japan since October, 2012, has shown that the unique features of this new *Catharanthus* plant are stable and reproduced true to type in successive generations.

SUMMARY OF THE INVENTION

Plants of the new *Catharanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Eld Stjarna'. These characteristics in combination distinguish 'Eld Stjarna' as a new and distinct *Catharanthus* plant:

1. Compact, semi-upright and uniformly mounding plant habit.
2. Vigorous growth habit.
3. Freely basal branching habit.
4. Freely flowering habit.

5. Long flowering period.
6. Relatively small star-shaped red purple-colored flowers that become light red with development.
7. Good garden performance.

Plants of the new *Catharanthus* can be compared to plants of the mutation parent selection. Plants of the new *Catharanthus* differ primarily from plants of the mutation parent selection in flower color as plants of the mutation parent selection have deep pink-colored flowers.

Plants of the new *Catharanthus* can be compared to plants of the *Catharanthus roseus* 'Suncatha 2460', disclosed in U.S. Plant Pat. No. 27,455. In side-by-side comparisons, plants of the new *Catharanthus* differ from plants of 'Suncatha 2460' in the following characteristics:

1. Plants of the new *Catharanthus* have shorter internodes than plants of 'Suncatha 2460'.
2. Plants of the new *Catharanthus* and 'Suncatha 2460' differ in flower color as plants of 'Suncatha 2460' have flowers that are light red purple in color.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph at the top of the sheet is a side perspective view of a typical flowering plant of 'Eld Stjarna' grown in a container.

The photograph at the bottom of the sheet is a close-up view of a typical flowering plant of 'Eld Stjarna'.

DETAILED BOTANICAL DESCRIPTION

The aforementioned photographs and following observations, measurements and values describe plants grown during the late summer and early autumn in 20-cm containers in an outdoor nursery in Higashiomi, Shiga, Japan and under cultural practices typical of commercial production. During the production of the plants, day temperatures averaged 25° C. and night temperatures averaged 15° C. Plants were four months old when the photographs were taken and five months old when the description was taken. In the following description, color references are made to The Royal Horticultural Society Colour Chart, 2015 Edition, except where general terms of ordinary dictionary significance are used.

Botanical classification: *Catharanthus roseus* 'Eld Stjarna'.

Parentage: Naturally-occurring branch mutation of a proprietary selection of *Catharanthus roseus* identified as code designation MP-mtl, not patented.

Propagation:

*Type*.—By vegetative tip cuttings.

*Time to initiate roots, summer*.—About two weeks at temperatures about 30° C.

*Time to initiate roots, winter*.—About three weeks at temperatures about 25° C.

*Time to produce a rooted young plant, summer*.—About five weeks at temperatures about 30° C.

*Time to produce a rooted young plant, winter*.—About six weeks at temperatures about 25° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, semi-upright and uniformly mounding plant habit; freely basal branching habit with numerous basal and secondary branches developing per plant; vigorous growth habit.

*Plant height*.—About 19 cm.

*Plant diameter*.—About 38 cm.

Lateral branch description:

*Length*.—About 30 cm.

*Diameter*.—About 5.3 mm.

*Internode length*.—About 5.9 mm.

*Strength*.—Strong.

*Aspect*.—Upright to outwardly.

*Texture*.—Pubescent.

*Color*.—Close to 145C.

Leaf description:

*Quantity and arrangement*.—About 16 per lateral branch; opposite, simple.

*Length*.—About 2.3 cm.

*Width*.—About 1.1 cm.

*Shape*.—Elliptical.

*Apex*.—Acute.

*Base*.—Rounded.

*Margin*.—Entire.

*Texture and luster, upper and lower surfaces*.—Pubescent.

*Venation pattern*.—Pinnate; reticulate.

*Color*.—Developing leaves, upper surface: Close to 137A. Developing leaves, lower surface: Close to 138A. Fully expanded leaves, upper surface: Close to NN137B; venation, close to 145C. Fully expanded leaves, lower surface: Close to 147B; venation, close to 145D.

*Petioles*.—Length: About 4.4 mm. Diameter: About 1.1 mm. Texture, upper and lower surfaces: Pubescent. Color, upper and lower surfaces: Close to 145C.

Flower description:

*Flower arrangement and habit*.—Single star-shaped salverform flowers arising from upper leaf axils; freely flowering habit with more than 250 to 300 small flowers developing per plant; flowers face mostly upright.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Individual flowers last about two to three days on the plant; flowers not persistent.

*Flower buds*.—Length: About 2.6 cm. Diameter: About 2.1 mm. Shape: Narrowly ovoid with cylindrical tube. Color: Towards the base, close to 145C tinged with close to 35D; mid-section, close to 145A; towards the apex, close to 49A.

*Flower diameter*.—About 2.6 cm.

*Flower length* (*depth*).—About 2.2 cm.

*Tube length*.—About 2 cm.

*Tube diameter, proximally*.—About 1.1 mm.

*Tube diameter, distally*.—About 1.9 mm.

*Corolla*.—Arrangement: Five petals in a single whorl fused at the base into a tube. Petal length from throat: About 1.3 cm. Petal width: About 5.6 mm. Petal shape: Narrowly elliptic to oblanceolate. Petal apex: Mucronate to acute. Petal margin: Entire. Petal texture, upper and lower surfaces: Smooth, glabrous. Throat texture: Smooth, glabrous. Tube texture: Smooth, glabrous. Color: Petal, when opening, upper surface: Close to 53C; eye, close to 53A. Petal, when opening, lower surface: Close to 54C; proximally, close to 56D. Petal, fully opened, upper surface: Close to 46C; eye, close to N45A; color does not change with development. Petal, fully opened, lower surface: Close to 50C, 52B and 56D; color does not change with development. Throat: Proximally, close to 145D; distally, close to 145A. Tube: Proximally, close to 145D tinged with close to 35C; distally, close to 145A.

*Calyx*.—Arrangement: Star-shaped tubular calyx with five sepals fused towards the base. Length: About 1.2 mm. Diameter: About 1.8 mm. Sepal length: About 1.5 mm. Sepal width: About 0.4 mm. Sepal shape: Lanceolate. Sepal apex: Acuminate. Sepal margin: Entire. Sepal texture, upper surface: Smooth, glabrous. Sepal texture, lower surface: Pubescent. Color, upper and lower surfaces: Close to 144B.

*Peduncles*.—Length: About 2 mm. Diameter: About 1 mm. Angle: Mostly upright. Strength: Strong. Texture: Pubescent. Color: Close to 145C.

*Reproductive organs*.—Stamens: Quantity per flower: Five. Anther size: About 1.2 mm by 0.5 mm. Anther shape: Narrowly elliptic. Anther color: Close to 8C. Pollen amount: Scarce. Pollen color: Close to 8C. Pistils: Quantity per flower: One. Pistil length: About 1.7 cm. Style color: Close to 145D. Stigma shape: Globose. Stigma color: Close to N144C. Ovary color: Close to 144A. Seeds and fruits: Seed and fruit development have not been observed on plants of the new *Catharanthus* to date.

Garden performance: Plants of the new *Catharanthus* have been observed to have good garden performance and to tolerate wind, rain and temperatures ranging from about 5° C. to about 35° C. to 40° C.

Pathogen & pest resistance: Plants of the new *Catharanthus* have not been observed to be resistant to pathogens and pests common to *Catharanthus* plants to date.

It is claimed:

1. A new and distinct *Catharanthus* plant named 'Eld Stjarna' as illustrated and described.

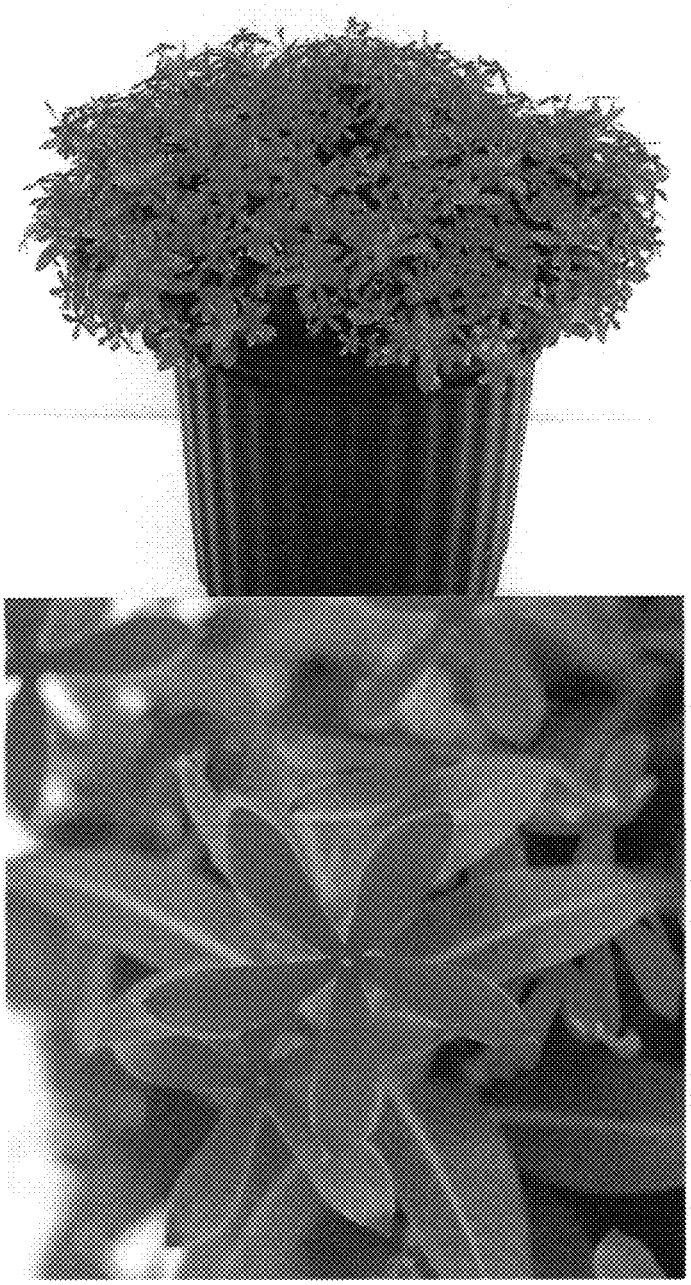

* * * * *